United States Patent [19]

Beach et al.

[11] Patent Number: 5,380,922
[45] Date of Patent: Jan. 10, 1995

[54] BENZENEDIMETHANOL SUITABLE FOR MICRONISATION

[75] Inventors: Steven F. Beach; David W. S. Latham; Tony G. Roberts; Colin B. Sidgwick, all of Ware, Great Britain

[73] Assignee: Glaxo Group Limited, London, England

[21] Appl. No.: 50,298

[22] Filed: May 14, 1993

[30] Foreign Application Priority Data

Nov. 29, 1990 [GB] United Kingdom ............... 9026005

[51] Int. Cl.⁶ ............................................. C07C 63/34
[52] U.S. Cl. ..................................................... 562/467
[58] Field of Search ........................................ 562/467

[56] References Cited

FOREIGN PATENT DOCUMENTS 2545482 11/1984 France.

Primary Examiner—Paul J. Killos
Attorney, Agent, or Firm—Bacon & Thomas

[57] ABSTRACT

1-Hydroxy-2-naphthalene carboxylate (hydroxynaphthoate) salt of 4-hydroxy-a$^1$-[[[6-(4-phenylbutoxy)hexyl]-amino]methyl]-1,3-benzendimethanol in the form of spherical accretions of microcrystals, the spherical accretions being free-flowing, friable and micronisable and preferably having a mean particle size of from 70 to 300 mm and a mean surface area from 4 to 12 m$^2$g$^{-1}$. The hydroxynaphthoate salt in the claimed form may be prepared by quenching a hot organic/aqueous organic solution containing the salt with a cold organic/aqueous organic solvent.

39 Claims, 2 Drawing Sheets

BENZENEDIMETHANOL SUITABLE FOR MICRONISATION

The present invention relates to a drug material suitable for micronisation. In particular, the invention relates to a novel readily micronisable form of the 1-hydroxy-2-naphthaleneearboxylate (hereinafter hydroxy naphthoate) salt of 4-hydroxy-$\alpha^1$-[[[6-(4-phenylbutoxy)hexyl]amino]methyl]-1,3-benzenedimethanol (hereinafter compound A) and to processes for the preparation of this novel form.

United Kingdom Patent Specification No. 2140800A (GB2140800A) relates to phenethanolamine derivatives having a selective stimulant action at beta-2 adrenoreceptors. The compounds may be used inter alia in the treatment of respiratory diseases associated with reversible airways obstruction, such as asthma and chronic bronchitis. In particular, GB2140800A describes compound A and its physiologically acceptable salts, especially (at Example 20) its hydroxy naphthoate salt. Compound A and its hydroxy naphthoate salt have been found to be particularly advantageous in the treatment of such respiratory diseases.

When treating patients suffering from respiratory conditions, it has been found most convenient to deliver the appropriate beta-2 stimulant directly to the site of action, either by inhalation or insufflation. In order to administer a drug via these routes, it is first necessary to provide the active ingredient as a fine powder having an appropriate particle size range. Material meeting the required particle size specification is generally obtained by micronisation of the drug substance, using, for example, a mill, such as a fluid-energy mill.

The present inventors have found that when the hydroxy naphthoate salt of compound A is prepared as described in GB2140800A, Example 20, crystals ar obtained that are extremely difficult to micronise to the required particle size range. These crystals are seen to adhere to the feed system (in the fluid energy mill) causing accumulation and ultimately blockage. This accumulation and blockage (of crystals) prevents efficient micronisation.

It is an object of the present invention to provide a novel, readily micronisable form of the hydroxy naphthoate salt of compound A that overcomes the disadvantage (in terms of micronisation) associated with the specific crystalline form described above.

According to the present invention, there is provided the hydroxy naphthoate salt of compound A in the form of spherical accretions of microcrystals, the spherical accretions being free-flowing, friable and micronisable.

The present inventors have surprisingly found that the presently claimed form of the hydroxy naphthoate salt of compound A, a form that combines a novel, spherical shape, and a free-flowing and friable nature, is readily micronisable to a material suitable for use in dosage forms that are administered by inhalation or insufflation.

The present invention provides the hydroxy naphthoate salt of compound A in the form of spherical accretions of microcrystals. This form consists of thin crystalline plates arranged radially about a central core or void. The form has an open structure in which the polymorphic form of the compound A hydroxy naphthoate is the same as that obtained from Example 20 of GB2140800A. The form provided by the present inventors also encompasses two or more spherical accretions (of microcrystals) fused together. In the present specification, the term "spherical" refers both to sphere shaped and spherelike (i.e. spheroidal) shaped forms. Spherelike forms would include elliptical (egg shaped) and distorted elliptical (pear shaped) forms.

The present novel form of the compound A hydroxy naphthoate must be free-flowing. This means that the form must flow freely into a powder mill, for example a fluid energy powder mill, to allow its efficient particle size reduction by micronisation on an industrial scale. The physical characteristics of a material that determine its flow characteristics include its bulk density, cohesivity, particle size and shape and uniformity with respect to the particle size.

Ideally, a material, in order to be free flowing, will have a high bulk density, a low cohesivity, and a uniform particle size distribution. To meet this ideal, the individual particles within the material should also be spherical in shape. The present novel form meets these criteria. Employing methods of measurement based upon those described by R. L. Carr in *Chemical Engineering*, 1965, 163–168 the present novel form exhibits a high aerated bulk density, preferably from 0.2 to 0.5 gml$^{-1}$, especially from 0.3 to 0.4 gml$^{-1}$, a low cohesivity, preferably from 0 to 20%, especially from 0 to 5%, a spherical (or near spherical) particle shape and a uniform particle size distribution, as measured by a uniformity coefficient of from 1 to 20, preferably of from 1 to 5, typically about 3.

The present novel form of the compound A hydroxy naphthoate must be friable. This means that the form must be easily broken down to particles of a size suitable for use in a pharmaceutical dosage form to be delivered by inhalation or insufflation.

The present novel form of the compound A hydroxy naphthoate must be micronisable. This means that the form must be easily broken down under micronising conditions, for example, in a fluid-energy mill, to particles of a size suitable for use in a pharmaceutical dosage form to be delivered by inhalation or insufflation.

The present novel form of the compound A hydroxy naphthoate preferably has a mean particle size of from 70 to 300 μm, most preferably from 100 to 200 μm, when measured by a laser diffraction method, T. Allen in Particle Size Measurement, 1981, 3rd Edition. The particle size distribution (measured by sieve analysis) is within the range 10 to 2000 μm, preferably from 100 to 1000 μm. For a discussion of sieve analysis, see the above Allen reference.

The present novel form of the compound A hydroxy naphthoate preferably has a mean surface area of from 4 to 12 m$^2$g$^{-1}$ most preferably from 6 to 10 m$^2$g$^{-1}$, when measured by the nitrogen adsorption method of Brunnauer, Emmett and Teller (BET), S. Lowell and J. E. Shields, Powder Surface Area and Porosity, 1984, 2nd Edition.

Conventional wisdom in the powder milling art suggests that, for optimum How properties, a material should consist of large particles having a low surface area. The present inventors have surprisingly found that, in the case of the preferred form of the compound A hydroxy naphthoate, a novel form that consists of large particles having a high surface area flows far more freely than a known form (GB2140800A, Example 20) that consists of large particles having a low surface area. This finding contradicts the conventional wisdom. A skilled man seeking to overcome the flow difficulties associated with the compound A hydroxy naphthoate would not have expected to produce a material having the novel form's preferred particle size/surface area properties.

Other favourable physical properties exhibited by the present novel form of the compound A hydroxy naphthoate are a low compressibility and a relatively low angle of repose. These terms are defined and their means of measurement are described by R. L.Carr in Chemical Engineering, 1965, 163–168. Preferably the present novel form has an angle of repose of from 25°–50°, especially from 40°–50°, and a compressibility of from 5 to 25%, especially 8 to 20%.

The provision of the present novel form of the compound A hydroxy naphthoate allows its efficient micronisation on an industrial scale. According to a further aspect of the present invention therefore, there is provided a process for the micronisation of the hydroxy naphthoate salt of compound A comprising feeding the hydroxy naphthoate salt of compound A in the form of spherical accretions of microcrystals, the spherical accretions being free-flowing, friable and micronisable into a microniser, micronising the hydroxy naphthoate salt to give a micronised material and collecting the micronised material.

Preferably the present novel form of the compound A hydroxy naphthoate is micronised until the collected material has a particle size range that is suitable for pharmaceutical dosage forms to be delivered by inhalation or insufflation. A suitable particle size range for this use is from 1 to 10 μm, preferably from 1 to μm.

The present novel form of the compound A hydroxy naphthoate may be prepared by any suitable method. In a still further aspect of the present invention, however, there is provided a process for the preparation of the hydroxy naphthoate salt of compound A in the form of spherical accretions of microcrystals, the spherical accretions being free-flowing, friable and micronisable said process comprising quenching an organic or aqueous organic solution of the hydroxy naphthoate salt of compound A with an organic or aqueous organic solvent having a lower temperature than the said solution, to give spherical accretions of microcrystals of the hydroxy naphthoate salt of compound A (the product) and collecting the product.

For brevity, the organic or aqueous organic solution will hereinafter be described as "hot" and the organic or aqueous organic solvent having a lower temperature will hereinafter be described as "cold", these are to be understood as relative and not absolute terms.

The production of large spherical shaped, crystalline material from the above crystallisation is extremely unusual and unexpected. The crystallisation, once initiated, is relatively fast. Such "fast" crystallisations usually lead to the production of a fine material having a small particle size.

In the above process, an "aqueous organic" solution or solvent contains up to about 10%(v/v) water. Preferably, a hot organic solution and a cold organic solvent are employed in the above process.

Preferably, the organic solvent employed in the hot organic or hot aqueous organic solution has a boiling point (at 760 mmHg) from 40° to 150° C., especially from 60° to 120° C. The compound A hydroxy naphthoate should be sparingly soluble or insoluble in the solvent when cold and soluble in the solvent when hot. Solvents suitable for use in the hot organic or hot aqueous organic solution include lower alkyl ($C_{1-4}$) alcohols such as methanol, ethanol and isopropanol, lower alkyl ($C_{1-4}$) ethers, such as methyl t-butylether, and lower alkyl ($C_{1-4}$) esters, such as ethyl acetate. In a particularly preferred embodiment of the present process, the organic solvent employed in the hot organic or hot aqueous organic solution is a lower alkyl alcohol, especially methanol, ethanol or isopropanol, most especially methanol.

In all of the above cases, the hot organic or the hot aqueous organic solution may contain a single solvent or-a mixture of solvents.

The organic solvent employed in the cold organic or cold aqueous organic solvent should be miscible with the organic solvent employed in the hot organic or hot aqueous organic solution. Preferably it has a freezing point from −150° to −20° C., especially from −130° to −50° C. The compound A hydroxy naphthoate should be sparingly soluble or insoluble in the solvent when cold. Solvents suitable for use in the cold organic or cold aqueous organic solvent include lower alkyl ($C_{1-4}$) alcohols, such as methanol, ethanol and isopropanol, lower alkyl ($C_{1-4}$) ethers, such as methyl t-butyl ether, and lower alkyl ($C_{1-4}$) esters, such as ethyl acetate. In a particularly preferred embodiment of the present process, the organic solvent employed in the cold organic or cold aqueous organic solvent is a lower alkyl alcohol, especially methanol, ethanol or isopropanol, most especially isopropanol.

In all of the above cases, the cold organic or the cold aqueous organic solvent may contain a single solvent or a mixture of solvents.

The temperature of the "hot" solution and the "cold" solvent are chosen to effect a fast crystallisation of the compound A hydroxy naphthoate, such that spherical accretions of microcrystals are formed. The temperatures employed will depend, in large measure, on the choice of solvent or solvents. Conveniently, the temperature of the hot organic or the hot aqueous organic solution is from 30° to 80° C., especially from 40° to 70° C. Also conveniently, the temperature of the cold organic or the cold aqueous organic solvent is form −35° to 15° C., especially from −25° to 10° C.

The hot organic or hot aqueous organic solution may be quenched either by addition to or by the addition of the cold organic or cold aqueous organic solvent. Preferably the hot organic or the hot aqueous organic solution is added to the cold organic or the cold aqueous organic solvent.

During this quenching process, it is preferable to maintain the temperature of the mixture ("hot" solution and "cold" solvent) at a temperature below about 20° C., especially from −10° to 20° C., most especially from 0° to 20° C. The mixture is maintained at a temperature within this range until all (or most of) the compound A hydroxy naphthoate has crystallised as spherical accretions of microcrystals. This crystallisation process can take, for example, from 10 to 120 min, in particular from 20 to 90 min.

The hydroxy naphthoate salt of compound A may be dissolved as such in the hot organic or the hot aqueous organic solution. Alternatively, the salt may be formed in situ by separately dissolving compound A and 1-hydroxy-2-naphthoic acid in the "hot" solution.

The starting material (compound A or the hydroxy naphthoate salt of compound A) for use in the above process may be prepared by the methods described in GB2140800A.

Once formed by the present process the spherical accretions of microcrystals may be collected by any suitable process, for example by filtration.

The contents of the references mentioned above, that is GB 2140800A; R L Carr, Chemical Engineering, 1965, 163–168; T Allen, Particle Size Measurement, 1981, 3rd Edition. S.Lowell and J E Shields, Powder Surface Area and Porosity, 1984, 2nd Edition, are hereby incorporated by way of reference.

BRIEF DESCRIPTION OF DRAWINGS

The present novel form of the hydroxy naphthoate salt of compound A processes for its preparation and processes for its micronisation will now be described by way of example only. In the Figures.

This figure also has an inset showing, in close up, the surface of a spherical accretion obtained by the process described in Example 8.

(A) Preparation of the Hydoxynaphthoate Salt of Compound A

Comparative Example

Figure 1:
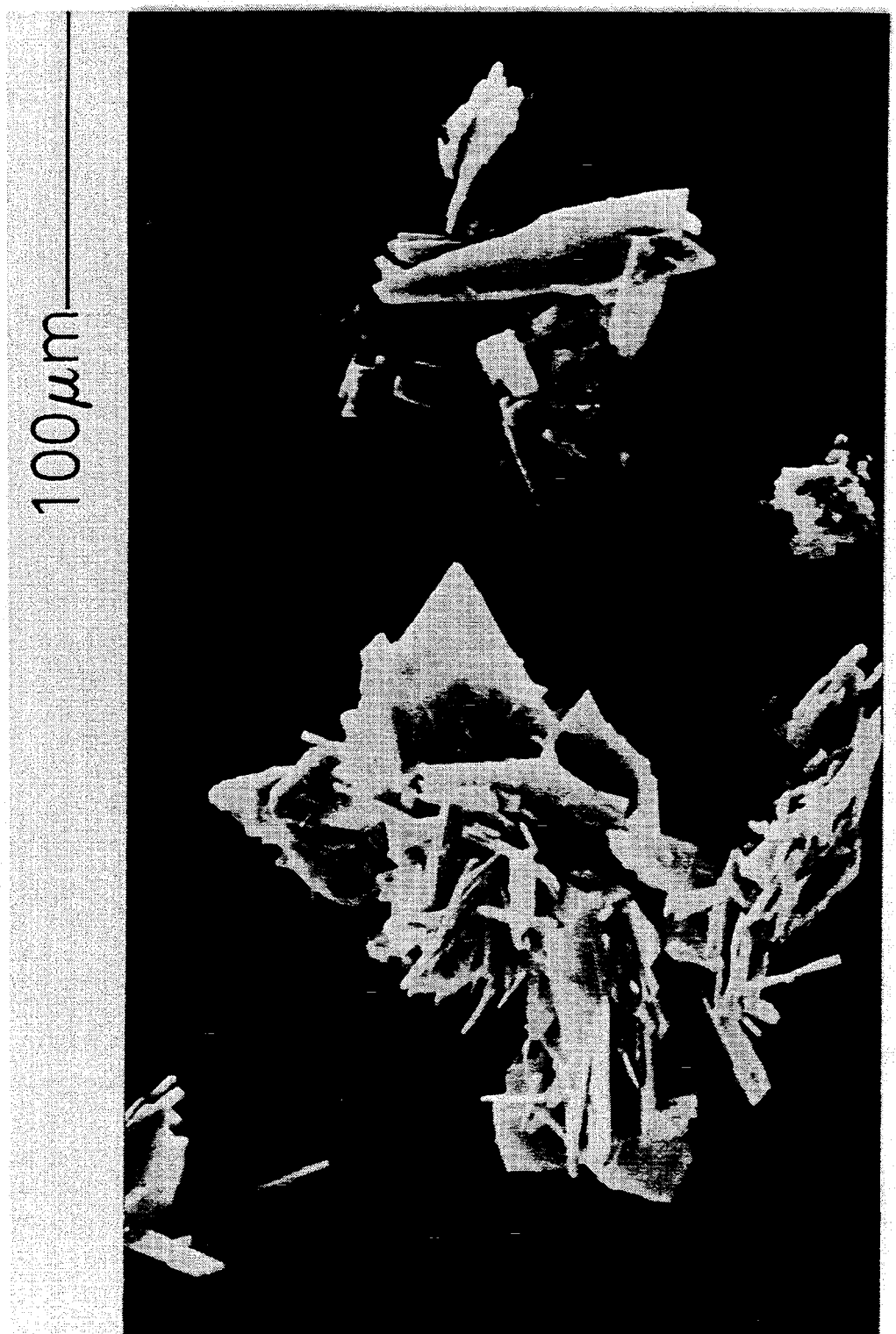
FIG. 1 is a scanning electron micrograph of the known crystalline form of the hydroxy naphthoate salt of compound A obtained by following the comparative Example set out below.

4-Hydroxy-$\alpha^1$-[[[6-(4-phenylbutoxy)hexyl]amino]methyl]-1,3-benzenedimethanol (compound A) was dissolved in hot ($>60°$) isopropanol. A solution of 1-hydroxy-2naphthoic acid (1 equiv.) in hot (70° C.) isopropanol was added. The mixture was seeded, allowed to cool to 40° C. (ca. 2 hr) and then further cooled to 5° C. (ca. 2 hr). The solid product was isolated by filtration, washed with cold isopropanol and dried in vacuo. The product obtained gave the scanning electron micrograph set out in FIG. 1.

Example 1

Cold (ca. −15° C.) isopropanol was added rapidly to a solution of the hydroxy naphthoate salt of compound A in hot (ca. 65° C.) isopropanol. The resulting suspension was allowed to stand at ca. 5° C. for 1 hr and the product was then collected by filtration, washed with cold isopropanol and dried in vacuo at 50° C.

Example 2

Cold (ca. −15° C.) isopropanol was added rapidly to a solution of the hydroxy naphthoate salt of compound A in hot (ca. 40° C.) methanol. The resulting suspension was allowed to stand at ca. 5° C. for 1 hr and the product was then collected by filtration, washed with cold isopropanol and dried in vacuo at 50° C.

Example 3

Compound A (4.63 kg) and 1-hydroxy-2-naphthoic acid (2.10 kg) were dissolved in hot (ca. 60° C.) methanol. The solution was added to cold (ca. 5° C.) isopropanol. During the addition the temperature of the "mixed" solution was allowed to increase until it reached 15° C., whereupon the mixture was maintained at 15° C. (±2° C.) 30 min., after which the product was isolated by filtration, washed with cold isopropanol and dried in vacuo at 40° C.

Example 4

A mixture of compound A (12.4 kg) and 1-hydroxy-2-naphthoic acid (5.6 kg) in hot (57°±3° C.) methanol was added to cold (below 15° C.) isopropanol (optionally containing up to 6% (v/v) water). During the addition the temperature of the mixture did not rise above 15°–20° C. The resulting suspension was stirred at about 20° C. for about 1 hr. The solid was then collected by filtration, washed with cold isoproparol and dried in vacuo at about 40° C.

Example 5

A solution of the hydroxy naphthoate salt of compound A in hot (ca. 70° C.) isopropanol (9.5 vol) was added over an 8 min. period to cold (5°–10° C.) t-butyl methyl ether (25 vol.) with stirring under nitrogen. After 30 min. (at ca. 5° C.) the solid material was isolated by filtration, washed with cold isopropanol and dried. The product obtained had a melting point of 121.5°–137.50° C.

Example 6

The hydroxy naphthoate salt of compound A was dissolved in hot (75° C.) isopropanol (9.5 vol.) under nitrogen and the solution was allowed to cool slowly with stirring to 57° C. Cold (−30° C.) isopropanol (14 vol.) was added to give a mixture the temperature of which was ca. 17° C. After about 4 hr. the solid product was filtered, washed with cold isopropanol and dried in vacuo.

Example 7

A hot (ca. 60° C.) solution of compound A and 1-hydroxy-2-naphthoic acid (1 equiv.) in methanol (5.8 vol.) was added during ca. 1 min. to cold (−10° C.) isopropanol (11.6 vol.) with stirring and the mixture was stirred at 0°–5° C. for 1.5 hr. The solid product was collected by filtration, washed with cold isopropanol and dried in vacuo.

Example 8

A hot (60° C.) solution of compound A and 1-hydroxy-2-naphthoic acid (1 equiv) in methanol (5.6 vol). was added during ca. 0.5 h to cold isopropanol. Throughout the mixing process, the temperature of the mixture was maintained in the range 12°–17° C. The mixture was stirred for 1 hr. at 15° C. and the solid product was then collected by filtration. The filter cake was washed with cold isopropanol and dried in vacuo at 40° C.

Figure 2:
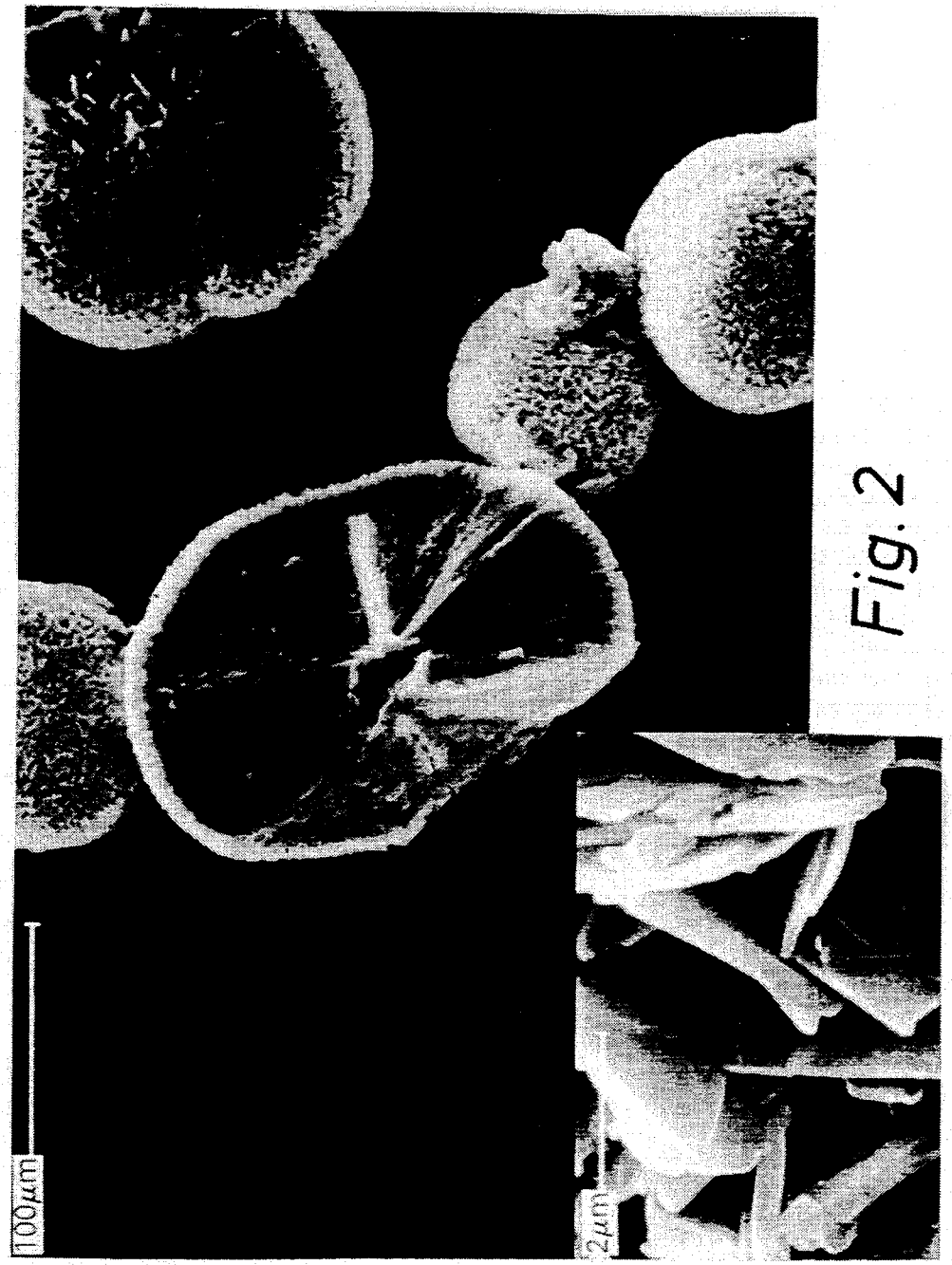
FIG. 2 is a scanning electron micrograph of the claimed form of the hydroxy naphthoate salt of compound A obtained by following Example 8 set out below.

The product obtained gave the scanning electron micrograph set out in FIG. 2. The microcrystalline nature of this novel form can be seen from the inset or FIG. 2 which shows in close up, the surface of one of the spherical accretions obtained.

(B) Physical Properties of Two Forms of the Hydroxynaphthoate Salt of Compound A The table set out below compares the physical properties of the known form of the hydroxy naphthoate salt (as prepared in the above comparative example) with the same properties of the present novel form of the hydroxy naphthoate salt (as prepared by the process described in Example 8).

TABLE

| Physical Property | Comparative Example | Example 8 |
| --- | --- | --- |
| Bulk Density (gml-1) | 0.16 | 0.30 |
| Compressibility (%) | 40 | 9.0 |
| Cohesivity (%) | 82 | 1.3 |
| Angle of Repose (Degrees) | 65 | 41 |
| Mean Particle size (μm) (Laser Analysis) | 26 | 156 |
| Mean Surface Area ($m^2 gm^{-1}$) (BET analysis) | 1.9 | 9.6 |

(c) Micronisation of Two Forms of the Hydroxynaphthoate Salt of Compound A

Micronisation takes place in a fluid energy microniser of known type. Suitable examples are described and illustrated in Remington's Pharmaceutical Sciences, 1985, 17th Edition, at p. 1588, the contents of which disclosure are hereby incorporated by way of reference. During micronisation, raw drug passes through a hopper and is carried through a venturi by a jet of air into a cyclone where the shearing action of air jets and collisions of drug particles break up the crystals. Micronised drug falls from the cyclone into a container; "fines" leave in the exhaust and are trapped in large "vacuum cleaner" bags.

(i) Micronisation of Comparative Example Material

During the micronisation of this material, a waxy deposit of drug built up on the wall of the venturi bringing the process to a halt after only a few minutes.

(ii) Micronisarion of Example 6 Material

During the micronisation of this material, it flowed smoothly from the hopper, through the venturi and into the cyclone. No waxy material adhered to the venturi in a running time of ca. 20 min.

We claim:

1. 1-Hydroxy-2-naphthalenecarboxylate salt of 4-hydroxy-$\alpha^1$-[[[6-(4-phenylbutoxy)hexyl]amino]methyl]-1,3-benzenedimethanol in the form of spherical accretions of microcrystals, the spherical accretions being free-flowing, friable and micronisable.

2. The hydroxynaphthoate salt according to claim 1 wherein the spherical accretions of microcrystals have a mean particle size from 70 to 300 μm.

3. The hydroxynaphthoate salt according to claim 1 wherein the spherical accretions of microcrystals have a mean surface area from 4 to 12 $m^2 g^{-1}$.

4. The hydroxynaphthoate salt according to claim 1 wherein the spherical accretions of microcrystals have a particle size distribution from 100 to 1000 μm.

5. The hydroxynaphthoate salt according to claim 1 wherein the spherical accretions of microcrystals have an aerated bulk density from 0.2 to 0.5 $gml^{-1}$.

6. The hydroxynaphthoate salt according to claim 1 wherein the spherical accretions of microcrystals have a cohesivity from 0 to 20%.

7. The hydroxynaphthoate salt according to claim 1 wherein the spherical accretions of microcrystals have a uniformity coefficient from 1 to 5.

8. The hydroxynaphthoate salt according to claim 1 wherein the spherical accretions of microcrystals have an angle of repose from 25° to 50°.

9. The hydroxynaphthoate salt according to claim 1 wherein the spherical accretions of microcrystals have a compressibility from 5 to 25%.

10. The hydroxynaphthoate salt according to claim 1 wherein the spherical accretions of microcrystals each comprise thin crystalline plates arranged radially about a central core or void.

11. A process for the micronisation of the 1-hydroxy-2-naphthalenecarboxylate salt of 4-hydroxy-$\alpha^{-1}$-[[[6-(4-phenylbutoxy)hexyl]amino]methyl]-1,3-benzenedimethanol comprising feeding the hydroxynaphthoate salt of 4-hydroxy-$\alpha^{-1}$[[[6-(4-phenylbutoxy)hexyl]amino]methyl]-1,3benzendimethanol in the form of spherical accretions of microcrystals, the spherical accretions being free-flowing, friable and micronisable, into a microniser, micronising the hydroxynaphthoate salt to give micronised material and collecting the micronised material.

12. A process for the preparation of the 1-hydroxy-2-naphthalenecarboxylate salt of 4-hydroxy-$\alpha^1$-[[[6-(4-phenylbutoxy)hexyl]amino]methyl]-1,3-benzendimethanol in the form of spherical accretions of microcrystals, the spherical accretions being free-flowing, friable and micronisable said process comprising quenching a hot organic or hot aqueous organic solution of the hydroxynaphthoate salt wit a cold organic or cold aqueous organic solvent to give spherical accretions of microcrystals of the hydroxynaphthoate salt and collecting said spherical accretions of microcrystals.

13. A process according to claim 12 wherein a hot organic solution of hydroxynaphthoate salt is quenched with a cold organic solvent to give spherical accretions of microcrystals of the hydroxynaphthoate salt.

14. A process according to claim 12 wherein the organic solvent employed in the hot organic or hot aqueous solution has a boiling point (at 760 mm Hg) from 40° to 150° C.

15. A process according to claim 14 wherein the organic solvent comprises a lower ($C_{1-4}$)alkyl alcohol, a lower ($C_{1-4}$) alkyl ether or a lower ($C_{1-4}$) alkyl ester.

16. A process according to claim 15 wherein the organic solvent comprises a lower alkyl alcohol.

17. A process according to claim 12 wherein the organic solvent employed in the cold organic or cold aqueous organic solvent has a freezing point from −150° to −20° C.

18. A process according to claim 17 wherein the organic solvent comprises a lower ($C_{1-4}$) alkyl alcohol, a lower ($C_{1-4}$) alkyl ether or a lower ($C_{1-4}$) alkyl ester.

19. A process according to claim 18 wherein the organic solvent comprises a lower alkyl alcohol.

20. A process according to claim 12 wherein the temperature of the hot organic or the hot aqueous solution is from 30° to 80° C.

21. A process according to claim 12 wherein the temperature of the cold organic or the cold aqueous solvent is from −35° to +15° C.

22. A process according to claim 12 wherein during the quenching of the hot organic or hot aqueous organic solution of the hydroxynaphthoate salt with the cold organic or cold aqueous organic solvent, the temperature of the mixture is maintained at a temperature below about +20° C.

23. A process according to claim 12 wherein the hot organic or hot aqueous solution of the hydroxynaphthoate salt is prepared by mixing 1-hydroxy-2-naphthoic acid and 4-hydroxy-$\alpha^1$-[[[6-(4-phenylbutoxy)hexyl]amino]methyl-1,3-benzenedimethanolin a hot organic or hot aqueous organic solvent.

24. The salt according to claim 2 wherein the mean particle size is from 100 to 200 μm.

25. The salt according to claim 3 wherein the mean surface is from 6 to 10 $m^2 g^{-1}$.

26. The salt according to claim 15 wherein the aerated bulk density is from 0.3 to 0.4 gml$^{-1}$.

27. The salt according to claim 6 wherein the cohesivity is from 0 to 5%.

28. The salt according to claim 7 wherein the uniformity coefficient is about 3.

29. The salt according to claim 8 wherein the angle of repose is from 40° to 50°.

30. The salt according to claim 9 wherein the compressibility is from 8 to 20%.

31. A process according to claim 14 wherein the boiling point is from 60° to 120° C.

32. A process according to claim 16 wherein the organic solvent comprises methanol, ethanol or isopropanol.

33. A process according to claim 32 wherein the organic solvent comprises methanol.

34. A process according to claim 17 wherein the freezing point is from −130° to −150° C.

35. A process according to claim 19 wherein the organic solvent comprises methanol, ethanol, or isopropanol.

36. A process according to claim 35 wherein the organic solvent comprises isopropanol.

37. A process according to claim 20 wherein the temperature is from 40° to 70° C.

38. A process according to claim 21 wherein the temperature is from −25° to +10° C.

39. A process according to claim 22 wherein the temperature is from −10° to +20° C.

* * * * *